United States Patent [19]

Pavia

[11] Patent Number: 4,910,312

[45] Date of Patent: * Mar. 20, 1990

[54] VARIOUS N-SUBSTITUTED 3-PIPERIDINE CARBOXYLIC ACIDS OR N-SUBSTITUTED 3-PYRIDINECARBOXYLIC ACIDS AND DERIVATIVES THEREOF

[75] Inventor: Michael R. Pavia, Ann Arbor, Mich.

[73] Assignee: Warner-Lambert Company, Morris Plains, N.J.

[*] Notice: The portion of the term of this patent subsequent to Sep. 20, 2005 has been disclaimed.

[21] Appl. No.: 207,688

[22] Filed: Jun. 16, 1988

Related U.S. Application Data

[63] Continuation-in-part of Ser. No. 110,052, Oct. 14, 1987, Pat. No. 4,772,615, which is a continuation of Ser. No. 927,908, Nov. 6, 1986, abandoned, which is a continuation-in-part of Ser. No. 897,308, Aug. 21, 1986, abandoned, and a continuation-in-part of Ser. No. 796,345, Nov. 8, 1985, abandoned.

[51] Int. Cl.$^4$ .............................................. C07D 211/32

[52] U.S. Cl. .................................. 546/227; 546/216; 546/213; 546/214; 546/215

[58] Field of Search ............... 546/227, 216, 213, 214, 546/275

[56] References Cited

FOREIGN PATENT DOCUMENTS 0066456 12/1982 European Pat. Off. .

OTHER PUBLICATIONS

EP Search Report attached.

Primary Examiner—Jane T. Fan
Attorney, Agent, or Firm—Joan Thierstein

[57] ABSTRACT

Selected analogs of nipecotic acid are the novel compounds of the present invention. The analogs are GABA uptake inhibitors for use to treat epilepsy and, thus, the invention is also pharmaceutical compositions and methods of use therefor.

16 Claims, No Drawings

VARIOUS N-SUBSTITUTED 3-PIPERIDINE CARBOXYLIC ACIDS OR N-SUBSTITUTED 3-PYRIDINECARBOXYLIC ACIDS AND DERIVATIVES THEREOF

This is a continuation-in-part of U.S. application Ser. No. 110,052, filed Oct. 14, 1987, now pending, which is a continuation of the U.S. application Ser. No. 927,908, filed Nov. 6, 1986, now abandoned, which is a continuation-in-part of U.S. application Ser. No. 897,308, filed Aug. 21, 1986, now abandoned, and U.S. application Ser. No. 796,345, filed Nov. 8, 1985, now abandoned.

BACKGROUND OF THE INVENTION

The present invention is novel compounds that are analogs of nipecotic acid. The present invention analogs are useful for analgesic, antipsychotic, anticonvulsant, antispastic, anxiolytic activity and antisymptomatic in Huntington's disease and Parkinsonism. Specifically, the anticonvulsant activity provides usefulness as broad spectrum antiepileptic agents.

Thus, the instant invention is also novel pharmaceutical compositions and methods of use for the novel compounds disclosed herein.

With regard to the anticonvulsant or antiepileptic utility, it is despite optimal use of the several antiepileptic drugs marketed in the United States that many patients with epilepsy fail to experience seizure control and others do so only at the expense of significant toxic side effects. In the early 1970's, no convincing evidence had been published that the primary antiepileptic drugs marketed in the US at that time controlled the seizures of more than 50% or improved more than 75% of the patients with epilepsy. The availability and use of several additional drugs since that time has brought improved seizure control to many patients. Notwithstanding the beneficial effects of the current drugs, there is still a need for new antiepileptic drugs with more selective anticonvulsant effect and less toxicity. R. L. Krall, et al, *Epilepsia*, 19:409 (1978).

N-(4,4-diphenyl-3-butenyl) nipecotic acid as well as nipecotic acid itself are among the known compounds compared for anticonvulsant effects by W. S. Schwark and W. Löscher in "Comparison of the Anticonvulsant Effects of Two Novel GABA Uptake Inhibitors and Diazepam in Amygdaloid Kindled Rats," *Naunyn Schmiedeberg's Arch. Pharmacol.*, 329:367–71 (1985).

In addition to Schwark and Löscher cited above, EP application 0066456 discloses that N-substituted azaheterocyclic carboxylic acids and their esters; i.e., 1-(diphenylalkyl)-3-piperidine carboxylic acid derivatives discussed above, inhibit neuronal and/or glial gamma-amino-butyric acid (GABA) uptake. The utility specifically disclosed for the compounds of EP 0066456 is for the treatment of anxiety, epilepsy, muscular and movement disorders, and mental and emotional disorders, as well as for analgesic and sedative effects.

The present invention compounds essentially differ from the compounds disclosed in EP application 0066456 by the moiety between a piperidine and aryl substituent. Thus, the present compounds are in no way taught therein.

SUMMARY OF THE INVENTION

The present invention relates to a compound of the formula (I)

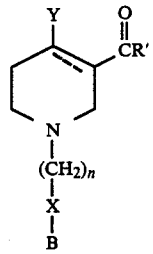

wherein
n is a positive integer of 1, 2, 3, or 4;
- - - - is a single or double bond;
Y is hydrogen, hydroxy, or alkyl of from one to four carbons, inclusive, with the proviso that when the - - - - is a double bond then Y is hydrogen or alkyl;
R' is hydroxy, lower alkoxy or $NR_1R_2$ wherein $R_1$ and $R_2$ are independently hydrogen or lower alkyl;
X is oxygen, $S(O)_z$ wherein z is 0, 1, or 2, or NR" wherein R" is hydrogen or lower alkyl;
B is (i)

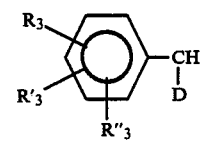

wherein $R_3$, $R'_3$, $R''_3$ are independently hydrogen, halogen trifluoromethyl, hydroxy, lower alkyl, lower alkoxy, $NR_5R_6$ wherein $R_5$ and $R_6$ are independently hydrogen or lower alkyl, or $SO_2NR_5R_6$ wherein $R_5$ or $R_6$ are defined above; and D is 2-or 3-thienyl, 2-, 3- or 4-pyridyl, or cycloalkyl of from five to seven ring carbons optionally substituted by alkyl of from one to four carbons, inclusive, particularly cyclohexyl, (ii)

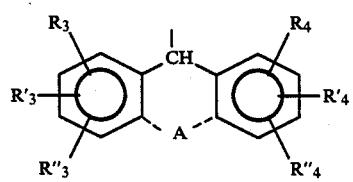

wherein $R_3$, $R'_3$, $R''_3$, $R_4$, $R'_4$, and $R''_4$ are independently hydrogen, halogen, trifluoromethyl, hydroxy, lower alkyl, lower alkoxy, $NR_5R_6$ wherein $R_6$ and $R_6$ are as defined above, or $SO_2NR_5R_6$ wherein $R_5$ ad $R_6$ are as defined above; and A is absent, completion of an optional bond, $-CH_2-$, $-CH_2CH_2-$, $-CH=CH-$, $-O-$, $-S(O)_z-$ wherein z is 0, 1, or 2, or $NR_7$ wherein $R_7$ is hydrogen or lower alkyl; or its diastereomers; or enantiomers;

and both pharmaceutically acceptable base salts an acid addition salts thereof.

Particularly, preferred compounds of this invention are those in which B is $I_2$ wherein A is absent.

The more preferred compounds of the present invention are compounds of formula I wherein Y is hydrogen, n is 2, X is oxygen, and B is $I_2$ wherein A is absent and $R_3$ and $R_4$ are halogen or trifluoromethyl and $R'_3$, $R''_3$, $R'_4$, $R''_4$ are all hydrogen. Additionally, among the more preferred compounds of formula I are those compounds, which, if possible, for example, when ---- is a single bond, is the R(-) optical isomer. That is, where two optical isomers exist because of an asymmetric carbon in the nitrogen containing ring of the compounds of formula I the R(-) optical isomers are the more active of the isomers.

The most preferred compound of the invention is the 1-[2-[bis[4-(trifluoromethyl)phenyl]methoxy]ethyl]-3-pyridinecarboxylic acid.

The compounds of formula I may form pharmaceutically acceptable salts with both organic and inorganic acids or bases.

For example, the acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of the invention may contain asymmetric carbon atoms. The invention includes the individual diastereomers, or enantiomers, and mixtures thereof. The individual diastereomers or enantiomers may be prepared or isolated by methods known in the art. For example, for preparation of an optically active carbon at position three of the piperidine in a compound of formula I, an optically active N-unsubstituted azaheterocyclic carboxylic acid or ester of formula III may be employed as a starting material in the reactions described herein to provide the resolved optically active carbon in the piperidinyl substituent. See Ackerman, A. N. and DeJungh, D. K., *Recevil traveaux de Chemiques*, 70:599-916 (1951).

The present invention also relates to a process for the preparation of the compounds of formula I which comprises reacting the appropriate compound of formula II having either chloro (Cl), bromo (Br) or OSO$_2$R wherein R is methyl, tolyl and the like, in the terminal position and wherein X, n and B are as defined above with an appropriately substituted piperidine having the formula III wherein ---- Y, and R' are as defined above, generally, according to the following scheme.

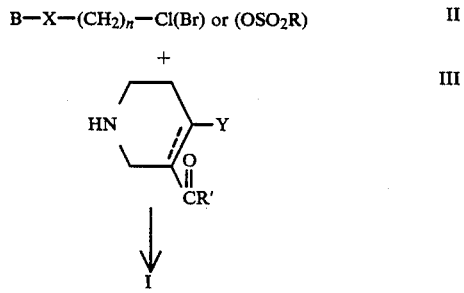

Under certain circumstances it is necessary to protect either the N or O of intermediates II and III in the above noted process with suitable protecting groups which are known. Introduction and removal of such suitable oxygen and nitrogen protecting groups are well known in the art of organic chemistry; see for example, (1) "Protective Groups in Organic Chemistry," J. F. W. McOmie, ed., (N.Y., 1973), pp. 43ff, 95ff; (2) J. F. W. McOmie, *Advances in Organic Chemistry*, 3:191-281 (1963); (3) R. A. Borssonas, *Advances in Organic Chemistry*, 3:159-190 (1963); and (4) J. F. W. McOmie, *Chem. & Ind.*, 603 (1979).

Examples of suitable oxygen protecting groups are benzyl, t-butyldimethylsilyl, methyl, isopropyl, ethyl, tertiary butyl, ethoxyethyl, and the like. Protection of an N—H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbamate, and the like.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

For example, the compounds of formula III may require R' to be replaced by a projecting group for the reaction shown in the scheme and then reacted to give compounds of formula I wherein R' is as defined above.

The products of the reactions described herein are isolated by conventional means such as extraction, distillation, chromatography, and the like. Generally, the starting materials are known, can be purchased commercially, or synthesized by known methods.

The present invention further includes a pharmaceutical composition comprising an analgesic, antipsychotic, anticonvulsant, antispastic, anxiolytic or antisymptomatic for Huntington's or Parkinson's disease effective amount of a compound of formula I together with a pharmaceutically acceptable carrier.

Finally, the present invention concerns a method for treating pain, psychosis, convulsions, seizures spasticity, anxiety, or muscular and movement disorders in mammals, including humans, suffering therefrom by administering to such mammals an effective amount of a compound of the formula I as defined above in unit dosage form.

DETAILED DESCRIPTION OF THE INVENTION

The term "halogen" as used herein in the definition of the compounds of formula I includes fluorine, chlorine, bromine, and iodine.

The term "lower" in reference to alkyl or alkoxy means a straight or branched chain of from one to four carbon atoms, inclusive, such as methyl, ethyl, propyl, isopropyl, n-butyl, sec-butyl, iso-butyl or tert-butyl and the like.

Generally, the compounds of formula I are prepared by refluxing a mixture of the compounds of formula II with compounds of formula III wherein R' is lower alkoxy in a solvent such as acetone, 2-butanone, N,N-dimethylformamide or the like, in the presence of a suitable base, such as sodium or potassium carbonate. The product, a compound of formula I wherein R' is lower alkoxy is, then, optionally converted to a compound of formula I wherein R' is hydroxy by treating with lithium hydroxide with methanol, ethanol, and the like as the solvent. Subsequently, compounds of formula I wherein R' is NR$_5$R$_6$ wherein R$_5$ and R$_6$ are as defined above may be prepared by methods analogous to those known for reacting organic acids with compounds of the formula HNR$_5$R$_6$.

The starting materials i processes described above to prepare the compounds of the formula I are generally known, commercially available or can be prepared by methods either known or analogous to known methods.

The compounds of formula I are tested for pharmacological activity using three procedures. The first is an assay for the uptake of the neurotransmitter gamma-amino-butyric acid (GABA) into slices of fat hippocampal (brain) tissue incubated in vitro analogous to those described by Johnston, G. A. R., et al in *J. Neurochem.* 26:1029-1032 (1976) entitled "Inhibition of the Uptake of GABA and Related Amino Acids in Rat Brain Slices by the Optical Isomers of Nipecotic Acid." Methods for this test are described in the following paragraph.

Male Long Evans rats (200-300 g) were sacrificed by decapitation, the brains quickly removed and the hippocampi were dissected out. Slices were cut (0.1×0.1 mm) on a McIlwain tissue chopper and dispersed in ice-chilled Krebs Ringer HEPES-buffered medium. Normal medium was composed of: NaCl (119 mM), KCl (4.75 mM), $CaCl_2$ (1.25 mM), $KH_2PO_4$ (1.20 mM), $MgSO_4$ (1.18 mM), HEPES (22 mM), EDA (0.03 mM), ascorbate (0.6 mM), and glucose (10 mM). The pH was adjusted to 7.2 with 3.0M Tris HCl. Following two washes in normal medium, 10 mg of tissue was incubated in a 3-ml volume of medium at 37° C. for 15 min in the presence or absence of test compound $^3$H-GABA (80.8 Ci/mmole; 0.05 μM final concentration) was added to each flask and the uptake was allowed to proceed for a two-minute period. At the end of the uptake period, samples were rapidly filtered through Whatman GF/F filters and washed once with 5 ml ice-chilled 0.9% sodium chloride. The filters with tissue were placed into scintillation vials with 2 ml $H_2O$ and allowed to sit for at least 60 min before scintillation fluid was added and samples counted. Blanks were treated in a manner similar to other samples, but were left on ice throughout the experiment. Results are expressed as percent control (no drug present) or $IC_{50}$ value.

Results with seven of the compounds tested are sown in the table below. These results demonstrate that all seven compounds inhibit the synaptic (sodium-dependent) uptake of GABA at concentrations that are relevant for pharmacological action.

TABLE I

GABA uptake into prisms of rat hippocampus in vitro in the presence of different concentrations of various synthetic compounds of formula I.

| Compound of Example | $IC_{50}$ (Calculated Median (50%) Inhibitory Concentration) |
|---|---|
| VII | 3.0 μM |
| VIII | 0.29 μM |
| VI | 11.0 μM |
| I | 12.0 μM |
| II | 35 μM (estim.) |
| IV | 60 μM (estim.) |
| X | 0.86 μM |
| XVII | 0.45 μM |
| XVIII | 0.7 μM |
| XIX | 0.1 μM |

The second pharmacological test, Threshold Maximal Electroshock, is an animal model for generalized seizures that is similar to that of Piredda, S.G. et al, "Effect of Stimulus Intensity on the Profile of Anticonvulsant Activity of Phenytoin, Ehtosuximide and Valproate, *The Journal of Pharmacology and Experimental Therapeutics*, 232, (3):741-45 (1985). The methods for this test are described in the following paragraph.

Male CF-1 mice (22-30 grams) are allowed free access to food and water prior to testing. For screening, groups of five mice are given a compound intraperitoneally at doses of 30, 100, and 300 mg/kg and tested at 0.5, 2.0, and 4.0 hr after dosing. Drugs are either dissolved in 0.9% saline or suspended in 0.2% methylcellulose. Animals are shocked with corneal electrodes (see below) and observed for tonic hindlimb exterior seizures. Absence of hindlimb extension is taken as an anticonvulsant effect.

The electroshock apparatus delivers a 60 Hz sine wave with a current amplitude of 14 mA (peak-to-peak) for 0.2 seconds. The current strength of 14 mA used in this procedure produces tonic extensor seizures in approximately 95% of untreated mice, but is only slightly above threshold for tonic extension.

Summaries of the number of animals protected from seizures when tested 30 minutes after administration of each compound of formula I, are given in Table II for two dose levels.

TABLE II

Threshold electroshock data

| Compound of Example | Number of Animals Protected from Seizures (n/5) | |
|---|---|---|
| | 100 mg/kg | 30 mg/kg |
| I | 3/5 | 0/5 |
| II | 4/5 | 1/5 |
| III | | 0/5 |
| VI | 1/5 | 0/5 |
| VII | 2/4 | ¼ |
| VIII | 4/5 | 4/5 |
| IX | 4/5 | 3/5 |
| XIII | 2/5 | 2/5 |
| X | 5/5 | 1/5 |
| XI | 2/5 | 1/5 |
| XVII | 4/5 | 4/5 |
| XVIII | 5/5 | 5/5 |
| XIX | 5/5 | 4/5 |

A third pharmacological test was performed as described in R. L. Krall et al, *Epilepsia*, 19:409 (1978), which is incorporated herein by reference. In this procedure, drugs were tested for attenuation of threshold clonic seizures in mice caused by subcutaneous administration of pentylnnetetrazol (85 mg/kg) which is a generally accepted model for absence type seizures. Results from the third test for the compound when administered either intraperitoneally (IP) or orally (PO) are shown below in Table III.

TABLE III

Effect of compounds of formula I in the subcutaneous pentylenetetrazol seizure test in mice.

| Compound of Example | Calculated Median Effective Dose ($ED_{50}$) | Time of Test (Following Dose) | Mode of Administration of the Compound to Mice |
|---|---|---|---|
| VII | 1.9 mg/kg | 30 min. | IP |
| VIII | 0.54 mg/kg | 120 min. | PO |
| XVII | 0.50 mg/kg | 120 min. | PO |

Thus, the activity of the compounds of formula I of value as pharmacological agents particularly for the treatment of seizures in animals, including humans, is shown by the above standard procedures. The term seizure means excessive and synchronized neuronal activity that disrupts normal neuronal function.

The compounds of structural formula I can be prepared and administered in a wide variety of dosage forms.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound of formula I. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methylcellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methyl cellulose, sodium carboxymethyl ellulose and other well-known suspending agents Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to about 300 mg per kilogram daily. A daily dose range of about 1 mg to about 50 mg per kilogram is preferred. The dosages, however, may be varied depending upon the requirements of the patient, the severity of the condition being treated and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrated the preferred methods for preparing the compounds of the invention.

PREPARATION I [(3-Bromopropoxy)methylene]-bis-bis[benzene](a compound of formula II wherein n is three, X is oxygen, 3 is $I_2$ wherein A is absent, and $R_3$, $R'_3$, $R''_3$, $R_4$, $R'_4$ and $R''_4$ are hydrogen). A solution of 20 g of 3-bromo-n-propanol in 50 ml of toluene is treated with 2 ml of concentrated $H_2SO_4$, warmed to 65° C., and treated dropwise at a temperature of 65° C. with a warm solution of 29.5 g diphenylmethanol. The mixture is stirred at 65° C. for 4 hr, cooled, washed with water, dried over $CaCl_2$, concentrated in vacuo and distilled at pump pressure to give the product, [3-bromopropoxy)methylene]-bis[benzene].

The NMR and analytical data is consistent with the product expected in Preparation I.

PREPARATION II [(2-Chloroethoxy)methylene]-bis-[benzene](a compound of formula II wherein n is 2, X is oxygen, B is $I_2$ wherein A is absent, and $R_3$, $R'_3$, $R''_3$, $R_4$, $R'_4$ and $R''_4$ are hydrogen). To 3.6 g 2-chloroethanol in 35 ml toluene at about 50° C. is added dropwise a warm solution of diphenylmethanol in 6.5 ml toluene over 40 min. The reaction contents are heated at 90° C. for 4 hr after final addition of the diphenylmethanol. Contents are cooled, $H_2SO_4$ is removed by washing the toluene layer with $H_2O$ three times, then dried over $CaCl_2$. Vacuum distillation of the residual oil after evaporation of toluene gives an oil of boiling point 130°-132° C. at 0.7 mm Hg. NMR spectrum is consistent with the expected product [(2-chloroethoxy)methylene]bis-[benzene]. This compound is used without further purification.

PREPARATION III [(2-Chloroethoxy)(3,4-chlorophenyl)(phenyl)]methane (a compound of formula II wherein n is 2, X is oxygen, B is $I_2$ wherein A is absent, $R_3$ and $R'_3$ are 3,4-dichloro and $R''_3$, $R_4$, $R'_4$ and $R''_4$ are hydrogen.

Step A 3,4-Dichlorobenzophenone (8.25 g) is placed in 100 ml EtOH at room temperature and $NaBH_4$ (0.33 g) is added to the solution The reaction is stirred for 3 hr. Thin layer chromatography (TLC) (silica gel; 20% ether, 80% hexane as eluent) indicates some ketone present. Approx. 0.1 g of additional $NaBH_4$ is added and the contents stirred for 30 min. When the benzophenone is completely consumed, a small amount of $H_2O$ is added to destroy excess $NaBH_4$. 1N LiOH is added, the solution heated on a steam bath for 10 min, cooled, then evaporated to a semisolid. The solid is dissolved in ether and washed with $H_2O$, brine, dried over $MgSO_4$, evaporated to an oil which is 98% pure by gas chromatography. The NMR spectrum corresponds well with expected product 3,4-dichloro-α-phenylbenzenemethanol. The product is used without further purification.

Step B

2-Chloroethanol (3.58 g) is dissolved in 50 ml of toluene in a 3-neck flask equipped with mechanical stirrer, dropping funnel, and a condenser. A catalytic amount (1 g) of concentrated $H_2SO_4$ is added to the toluene solution, then the mixture heated to 55° C. A toluene (15 ml) solution of 3,4-dichloro-α-phenylbenzenemethanol (7.5 g) as prepared in Step A is added dropwise over 30 min, then the total contents heated at 85° C. for 12 hr. The reaction mixture is cooled, diluted with toluene, washed with H₂O, brine, dried over MgSO₄, and evaporated to 9.45 g of an oil. This oil is 90% pure by gas chromatography and the NMR spectrum is consistent with that expected of [(3-chloroethoxy)(3,4-dichloropheyyl)(phenyl)]methane. Product is used without further purification.

PREPARATION IV 2-[(Diphenylmethyl)thio]ethanol (a compound of formula II wherein n is 2, X is sulfur, B is I₂ wherein A is absent, R₃, R'₃, R"₃, R₄, R'₄ and R"₄ are hydrogen). Potassium t-butoxide (2.24 g) is added to the thiol, α-phenylbenzenemethanethiol (4 g), dissolved in 40 ml of EtOH. To this stirred solution at reflux temperature is added very slowly over 50 min 2-chloroethanol (1.61 g). This mixture is refluxed for another 30 min. The mixture is cooled and filtered. The EtOH is evaporated and the remaining oil chromatographed on silica (30% ethyl acetate: 70% hexane as eluent). 3.6 g of the desired product, 2-[(diphenylmethyl)thio]ethanol, is obtained. M.P. 35° C.

EXAMPLE I

3-Piperidinecarboxylic acid 1-[2-[bis-(4-chlorophenyl)methoxy]ethyl]-, ethyl ester, (a compound of formula I wherein Y is hydrogen, R' is ethoxy, n is 2, X is oxygen, B is I₂ wherein A is absent, and R₃ and R₄ are each 4-chloro, R'₃, R"₃, R'₄ and R"₄ are hydrogen). The [(2-chloroethoxy)-methylene]bis[4-chlorobenzene] as prepared in PREPARATION II above (11.02 g), ethyl 3-piperidinecarboxylate (5.49 g), KI (0.3 g), and K₂CO₃ (9.73 g) are placed in 120 ml acetone and refluxed for about 63 hr. TLC (silica, 30% ethyl acetate: 70% hexane as eluent) is used to monitor completion of reaction. The contents are cooled, and acetone is removed. The residual oil is dissolved in ether, and washed with H₂O, brine, then dried over MgSO₄. The ether is evaporated to an oil (16 g) which is chromatographed on silica using 25% ethyl acetate: 75% hexane as eluent. 8.13 g of the desired product, 3-piperidinecarboxylic acid, 1-[2-[bis(4-chlorophenyl)methoxy]ethyl]-, ethyl ester, is obtained for a 55% yield. NMR spectrum is consistent with that expected for product.

| | | C | H | N | $Cl_{Total}$ |
|---|---|---|---|---|---|
| Elemental Analysis | Calc | 63.31 | 6.24 | 3.21 | 16.25 |
| | Found | 62.88 | 6.35 | 3.02 | 15.85 |

EXAMPLE II

3-Piperidinecarboxylic acid, 1-[2-(diphenylmethoxy)ethyl]-, ethyl ester, (a compound of formula I wherein Y is hydrogen, R' is ethoxy, n is 2, X is oxygen, and B is I₂ wherein A is absent, R₃, R'₃, R"₃, R₄, R' and R"₄ are hydrogen). The [(2-chloroethoxy)methylene]bis[benzene]as prepared above in PREPARATION II (4.37 g), ethyl 3-piperidinecarboxylate (2.78 g), K₂CO₃ (4.92 g), and KI (0.07 g) in acetone is refluxed for five days. TLC (silica, 30% ethyl acetate: 70% hexane as eluent) indicates product formation but a significant amount of unreacted halide is present. Contents are filtered, acetone evaporated to an oil which is chromatographed on silica (25% ethyl acetate: 75% hexane as eluent). The NMR corresponds to the proposed structure. After chromatography 1.8 g of 3-piperidinecarboxylic acid, 1-[2-(diphenylmethoxy)ethyl]-, ethyl ester is obtained.

| | | C | H | N |
|---|---|---|---|---|
| Elemental Analysis | Calc | 75.17 | 7.95 | 3.81 |
| | Found | 75.40 | 7.92 | 3.99 |

EXAMPLE III

3-Piperidinecarboxylic acid, 1-[3-(diphenylmethoxy)propyl]-, ethyl ester, monohydrochloride, (a compound of formula I wherein Y is hydrogen, R' is ethoxy, X is oxygen, n is 3, B is I₂ wherein A is absent, R₃, R'₃, R"₃, R₄, R'₄ and R"₄ are hydrogen) A mixture of [(3-bromopropoxy)methylene]bis[benzene]as prepared in PREPARATION I above (10 g), ethyl 3-piperidinecarboxylate (5.2 g), K₂CO₃ (10 grams), KI (0.1 g) in acetone (150 ml) is heated and stirred at reflux temperature, and monitored for completion of the reaction by TLC (silica gel). The mixture is refluxed for 30 hr, cooled, filtered, and the filtrate concentrated in vacuo to a yellow oil (15 g). The oil is triturated with petroleum ether (PE), filtered, and the PE solution concentrated to 8 g clear, colorless oil. The oil is purified by silica gel column chromatography (10% diethyl ether: 90% hexane as eluent) to give 4.5 g oil. NMR spectrum is consistent with expected product. Then 1.5 g oil is dissolved in isopropanol treated with isopropanol.HCl, diluted with ether, cooled, filtered, dried in vacuo at 40° C. to give the desired product, 3-piperidinecarboxylic acid, 1-[3-diphenyl-methoxy)propyl]-, ethyl ester monohydrochloride, M.P. 157°-158° C.

| | | C | H | N |
|---|---|---|---|---|
| Elemental Analysis | Calc. | 68.97 | 7.72 | 3.35 |
| | Found | 69.05 | 7.74 | 3.33 |

EXAMPLE IV

3-Piperidinecarboxylic acid, 1-[2-[(diphenylmethyl)thio]ethyl]-, ethyl ester, (a compound of formula I wherein Y is hydrogen, R' is ethoxy, n is 2, X is sulfur, B is I₂ wherein A is absent, and R₃, R'₃, R"₃, R₄, R'₄ and R"₄ are hydrogen). 2-[(Diphenylmethyl)thio]ethanol (3 g) as prepared in PREPARATION IV above is dissolved in 25 ml of CH₂Cl₂. Then triisopropyl amine (3.2 g) is added and the mixture cooled to −10° C. Methanesulfonyl chloride (1.4 g) is added and the mixture stirred at −10° C. for 1 hr and then at room temperature for four days. The solvent is evaporated and the remaining oil chromatographed on silica using 70% hexane: 30% ethyl acetate: 2% triethylamine as eluent. 2.5 g of the pure product, 3-piperidinecarboxylic acid, 1-[2-[(diphenylmethyl)thio]ethyl]-, ethyl ester, is obtained, M.P. 58–65° C. Yield: 55%. The NMR spectrum is consistent with the expected product.

| | | C | H | N |
|---|---|---|---|---|
| Elemental Analysis | Calc. | 72.02 | 7.62 | 3.65 |
| | Found | 71.92 | 7.70 | 3.43 |

EXAMPLE V

3-Piperidinecarboxlic acid, 1-[2-[(3,4-dichlorophenyl)]phenylmethoxy]ethyl, ethyl ester, (a compound of formula I wherein Y is hydrogen, R' is ethoxy, n is 2, X is oxygen, B is I₂ wherein A is absent, R"₃, R₄, R'₄, R''4 are hydrogen and R3 and R'3 are 3,4-dichloro). Ethyl 3-piperidinecarboxylate (4.25 g), and [(2-chloroethoxy)(3,4-chlorophenyl)(phenyl)]methane (8.5 g) are dissolved in N,N-dimethylformamide (DMF) (100 ml) and heated at 100° C. in the presence of $K_2CO_3$ (9.33 g) and a catalytic amount of KI (0.5 g). The reaction mixture is heated for about 17 hr. Chromatography (silica; 98% $CHCl_3$, 2% methanol-eluent) gives 7.3 g of product. The impure oil is chromatographed again on silica using an eluent consisting of 75% $CHCl_3$: 25% ethyl acetate. 5.38 g of light yellow oil is obtained. NMR spectrum of the oil corresponds to the expected product, 3-piperidinecarboxylic acid, 1-[2-[(3,4-dichlorophenyl)phenylmethoxy]ethyl], ethyl ester.

|  |  | C | H | N | $Cl_{Total}$ |
|---|---|---|---|---|---|
| Elemental Analysis | Calc. | 63.31 | 6.24 | 3.21 | 16.25 |
|  | Found | 63.14 | 6.18 | 3.24 | 16.23 |

EXAMPLE VI

3-Piperidinecarboxylic acid, 1-[3-diphenylmethoxy)-propyl]-, monohydrochloride, (a compound of formula I wherein Y is hydrogen, R' is hydroxy, n is 3, X is oxygen, B is $I_2$ wherein A is absent, and R3, R'3, R''3, R4, R'4 and R''4 are hydrogen). The hydrobromide salt of 3-peperidinecarboxylic acid, 1-[3-(diphenylmethoxy)-propyl]-, ethyl ester (15 g) as from EXAMPLE III above is dissolved in water an treated with $NaHCO_3$ to generate free base, which is extracted into ether, dried, concentrated to 10 g oil. The concentrate is dissolved in 100 ml MeOH and treated with 11.8 ml of 1N LiOH, stirred at room temperature for 24 hr, concentrated in vacuo, adjusted to pH 6.5 with 5% $NaH_2PO_4$ solution, extracted into 2×50 ml n-BuOH, the extracts concentrated in vacuo, then cyclohexane is added to the solid and reevapoated. The resulting solid is dried in an oven overnight at 35° C., triturated with diethyl ether and decanted two times. The HCl salt is prepared and dried. NMR spectrum is consistent with the expected product, 3-piperidinecarboxylic acid, 1-[3-(diphenylmethoxy)-propyl]-, monohydrochloride.

EXAMPLE VII

3-Piperidinecarboxylic acid, 1-[2-(diphenylmethoxy)ethyl]-, monohydrochloride, (a compound of formula I wherein Y is hydrogen, R' is hydroxy, n is 2, X is oxygen, B is $I_2$ wherein R3, R'3, R''3, R4, R'4 and R''4 are hydrogen, and A is absent). To 3-piperidinecarboxylic acid, 1-[2-(diphenylmethoxy)ethyl]-, ethyl ester obtained as an oil in EXAMPLE II above, is added slightly more than one equivalent of aqueous 1N LiO. Methanol is used as co-solvent. The contents are stirred for 24 hr, solvent removed to afford a semi-solid. 5% aqueous $NaH_2PO_3$ is added until a pH of 6.5 is obtained. This solution is then extracted with n-BuOH and dried, evaporated to a semisolid. The material is then converted to its HCl salt upon addition of isopropanolic HCl. Evaporation of isopropanol produced a solid which is recrystallized from EtOH-diethyl ether to give the desired product, -piperidinecarboxylic acid, 1-[2-(diphenylmethoxy)- propyl-, monohydrochloride having a M.P. 180°–182° C.

EXAMPLE VIII

3-Piperidinecarboxylic acid, 1-[2-[bis-4-(chlorophenyl)methoxy]ethyl]monohydrochloride, (a compound of formula I wherein Y is hydrogen, R' is hydroxy, n is 2, X is oxygen, B is $I_2$ wherein A is absent, R3 and R4 are each 4-chyloro and R'3, R''3, R'4 and R''4 are hydrogen). To 3-piperidinecarboxylic acid, 1-[2[bis(4-chlorophenyl)methoxy]ethyl]-, ethyl ester (2 g), obtained as an oil in the above EXAMPLE I is added 1.1 equiv. of 1N LiOH solution and MeOH. The solution is stirred at room temperature for 4 hr. The solution is concentrated and added to this is 5% aqueous $NaH_2PO_4$ until a pH of 65 is obtained. This aqueous solution is then extracted with n-BuOH, dried over $Na_2SO_4$, then evaporated to a semi-solid. Isopropanolic HCl is added to generate HCl salt, isopropanol evaporated to generate a solid which is recrystallized from EtOH-diethyl ether. This gives the desired product, 3-piperidinecarboxylic acid, 1-[2-[bis(4-chlorophenyl)methoxy]ethyl]monohyrochloride having a M.P. 151°–152° C.

EXAMPLE IX

3-Piperidinecarboxylic acid, 1-[2-[(3,4-dichlorophenyl)phenylmethoxy]ethyl]-, monohydrochloride (a compound of formula I wherein Y is hydrogen, R' is hydroxy, n is 2, X is oxygen, and B is $I_2$ wherein A is absent, and R3, R''3, R4, R'4 and R''4 are hydrogen and R'3 and R''3 are 3,4-dichloro). 5.38% g of the 3-piperidinecarboxylic acid, 1-[2-[(3,4-dichlorophenyl)-phenylmethoxy]ethyl]-, ethyl ester as prepared in EXAMPLE V above is dissolved in ethanol (40 ml) and 1N LiOH (18.5 ml) and stirred at room temperature for about 30 hr. Insolubles are filtered then the filtrate is evaporated in vacuo to leave a solid which is dissolved in $H_2O$, and the pH adjusted to 6.0 with 5% aqueous $NaH_2PO_4$. An oil is separated upon acidification. The acidified suspension is extracted with $CHCl_3$ which is then filtered. Removal of $CHCl_3$ and treatment with excess isopropanolic HCl then gives a solid after removal of the solvent. The solid is stirred in EtOAc at room temperature, then decanted and dried leaving a solid, 3-piperidinecarboxylic acid, 1-[2-[(3,4-dichlorophenyl)phenylmethoxy]ethyl]monohydrochloride having a M.P. 131°–138° C.

|  |  | C | H | N | $Cl_{Total}$ |
|---|---|---|---|---|---|
| Elemental Analysis | Calc. | 56.71 | 5.44 | 3.15 | 23.91 |
|  | Found | 56.75 | 5.42 | 3.09 | 23.73 |

EXAMPLE X

3-Piperidinecarboxylic acid, 1-[2-[4-chloro-3-(trifluoromethyl)phenyl]phenyl]methoxy]ethyl-, (a compound of formula I wherein Y is hydrogen, R' is hydroxy, n is 2, X is oxygen, and B is $I_2$ wherein A is absent, R3 is 4-chloro, R'3 is 3-trifluoromethyl, R''3, R4, R'4 and R''4 are hydrogen).

A. Benzene methanol, 4-chloro-3-trifluoromethyl-α-phenyl-.

Magnesium (0.46 g) chips are covered with about 5 ml of dry tetrahydrofuran to which 1-bromo-4-chloro-3-trifluoromethyl benzene (2.87 ml) in 15 ml dry tetrahydrofuran is added dropwise. After the magnesium is consumed excess benzaldehyde in 10 ml dry tetrahydrofuran is added to the Grignard product mixture prepared from the magnesium. This mixture is stirred at reflux for 18 hr. The reaction mixture is cooled and poured onto 50 ml saturated $NH_4Cl$ solution The organic layer is separated, dried over $MgSO_4$ and evaporated. The remaining oil is chromatographed on dry silica using 80% hexane: 20% ethyl acetate: 1% methanol as eluent. 3.6 g of the product, benzene methanol, 4-chloro-3-trifluoromethyl-α-phenyl-, (65% yield is obtained.

B. Benzene, 1-chloro-4-[(2-chloroethoxy)phenylmethyl]-2-(trifluoromethyl)-, (a compound of formula II wherein X is oxygen, n is 2, B is $I_2$ wherein A is absent, $R_3$ is 4-chloro and $R'_3$ is 3-trifluoromethyl, $R''_3$, $R_4$, $R'_4$ and $R''_4$ are hydrogen).

To a mechanically stirred solution of benzene methanol, 4-chloro-3-trifluoromethyl-α-phenyl- (3.6 g) that is prepared as described above in Part A and 0.3 ml of $H_2SO_4$ in 5 ml of toluene at 60° C. is added a solution of 2-chloroethanol in 10 ml of toluene dropwise for 30 min. The mixture is stirred at 80° C. for 3 hr, then the mixture is cooled and washed with 50 ml of water. The organic phase is separated, dried over $MgSO_4$ and evaporated. 4.1 g of the crude product, benzene, 1-chloro-4-[(2-chloro-ethoxy)phenylmethyl]-2-(trifluoromethyl)-, is obtained for a yield of 94% and used without further purification.

C. 3-Piperidinecarboxylic acid, 1-[2-[[4-chloro-3-(trifluoromethyl)phenyl]phenylmethoxy]ethyl]-, (a compound of the formula I wherein Y is hydrogen, R' is hydroxy, n is 2, X is oxygen, and B is $I_2$ wherein A is absent, $R_3$ is 4-chloro and $R'_3$ is 3-trifluoromethyl, $R''_3$, $R_4$, $R'_4$ and $R''_4$ are hydrogen).

The benzene, 1-chloro-4-[(2-chloroethoxy)phenylmethyl]-2-(trifluoromethyl)- as prepared above in part B. (4.1 g) is dissolved in 25 ml 2-butanone to which ethyl 3-piperidinecarboxylate (1.9 g) is added at once. $K_2CO_3$ (3.3 g) is added along with a small amount of NaI. The mixture is refluxed for 72 hr, then cooled, filtered and evaporated. An oil remains that is chromatographed on dry silica using 70% hexane, 30% ethyl acetate: 2% triethylamine as eluent. 4.2 g of the pure ester, 3-piperidinecarboxylic acid 1-[[4-chloro-3-(trifluoromethyl)phenyl]phenylmethoxy]ethyl]-, ethyl ester. (81% yield) is obtained.

D. 3-Piperidinecarboxylic acid, 1-[2-[[4-chloro-3-(trifluoromethyl)phenyl]phenylmethoxy]ethyl]-, hydrochloride salt, (a compound of the formula I wherein Y is hydrogen, R' is hydroxy, n is 2, X is oxygen, and B is $I_2$ wherein A is absent, $R_3$ is 4-chloro, $R'_3$ is 3-trifluoromethyl an $R''_3$, $R_4$, $R'_4$ and $R''_4$ are hydrogen).

3-Piperidinecarboxylic acid, 1-[2-[[4-chloro-3-(trifluoromethyl)phenyl]phenylmethoxy]ethyl]-, ethyl ester (4.2 g) as prepared above in Part C is dissolved in 2.5 ml of methanol to which 10 ml of 1N lithium hydroxide is added at once. The mixture is stirred overnight. Purified product is converted to a hydrochloride chloride salt and recrystallized from ethyl acetate for a 90% yield of 3-piperidinecarboxylic acid, 1-[2-[[4-chloro-3-(trifluoromethyl)phenyl]phenylethoxy]ethyl]-, monohydrochloride salt. M.P. 120°-127° C.

EXAMPLE XI

3-Piperidinecarboxylic acid, 1-[2-[(5H-dibenzo[a,d]cyclohepten-5-yloxy)ethyl]]-, (a compound of formula I wherein Y is hydrogen, R' is hydroxy, n is 2, X is oxygen, and B is $I_2$ wherein $R_3$, $R'_3$, $R''_3$, $R_4$, $R'_4$ and $R''_4$ are hydrogen and A is —CH=CH—).

A. 5H-Dibenzo[a,d]cyclohepten-5-ol.

5H-Dibenzo[a,d]cyclohepten-5-one (10 g) is dissolved in 80 ml of isopropyl alcohol and sodium borohydride (1.8 g) is added at once. The mixture is stirred at room temperature for two hr. 5 ml of water are added to quench the reaction and the solvent is evaporated. The residue is taken up in diethyl ether and washed with water, dried over $MgSO_4$ and evaporated. 9.8 g (98% yield) of 5H-dibenzo-[a,d]-cyclohepten-5-ol is obtained.

B. Ethanol, 2-(5H-dibenzo[a,d]cyclohepten-5-yloxy)-.

Under argon, 5H-dibenzo[a,d]cyclohepten-5-ol as prepared in Part A above (4 g) is dissolved in 50 ml dry tetrahydrofuran to which NaH (0.5 g) is slowly added at room temperature. Then neat ethyl 2-bromo acetate (3.21 g) is also slowly added. After stirring for several hours a suspension of 0.76 g of lithium aluminum hydride (LAH) in 100 ml diethyl ether is slowly added to this suspension and then stirred at room temperature for 20 min. Ethanol and water are added to quench the reaction. The mixture is filtered and evaporated. The residue is chromatographed over silica using 50% pentane: 50% diethyl ether as eluent. 2.9 g (80% yield) of the product, ethanol, 2-(5H-dibenzo[a,d]cyclohepten-5-yloxy)-, is obtained.

C. 3-Piperidinecarboxylic acid, 1-[2-[(5H-dibenzo[a,d]cyclohepten-5-yloxy)ethyl]], ethyl ester, (a compound of formula I wherein Y is hydrogen, R' is ethoxy, is 2, X is oxygen, and B is $I_2$ wherein $R_3$, $R'_3$, $R''_3$, $R_4$, $R'_4$ and $R''_4$ are hydrogen, and A is —CH=CH—).

Ethanol, 2-(5H-dibenzo[a,d]cyclohepten-5-yloxy)-, as prepared in Part B above (2 g) is dissolved in 40 ml of dry tetrahydrofuran to which triethylamine (1.7 g) is added at once. Methanesulfonyl chloride (0.014 g) is added dropwise ad the mixture stirred for 20 min, after which it is filtered and evaporated. Then the methanesulfonate is dissolved in 80 ml of 2-butanone to which ethyl 3-piperidinecarboxylate (1.9 g) is added at once. 3.3 g of $K_2CO_3$ are added and the mixture refluxed overnight, then cooled, filtered and evaporated. The remaining oil is chromatographed on dry silica using70% hexane: 30% ethyl acetate: 2% triethylamine as eluent. 3.4 g (75% yield) of 3-piperidinecarboxylic acid, 1-[2-[5H-dibenzo[a,d]cyclohepten-5-yloxy)ethyl]], ethyl ester is obtained.

D. 3-Piperidinecarboxylic acid, 1-[2-[(5H-dibenzo[a,d]cyclohepten-5-yloxy)ethyl]]-, (a compound of the formula I wherein Y is hydrogen, R' is hydroxy, n is 2, X is oxygen, B is $I_2$ wherein $R_3$, $R'_3$, $R''_3$, $R_4$, $R'_4$ and $R''_4$ are hydrogen, and A is —CH=CH—).

The ethyl ester of 3-piperidinecarboxylic acid, 1-[2-[(5H-dibenzo[a,d]cyclohepten-5-yloxy)ethyl]], (3.4 g) is dissolved in 25 ml of methanol and then 10 ml of 1N lithium hydroxide is added to the solution. The mixture is stirred at room temperature overnight. Purified product obtained as in Example IX above, 3-piperidinecarboxylic acid, 1-[2-[(5H-dibenzo-[a,d]cyclohepten-5-yloxy)ethyl]]-, is recrystallized from ethyl acetate to obtain 2.9 g of the product (92% yield). M.P. 152°-153° C.

Using appropriate methods from among those described above and using corresponding starting materials as required to obtain the desired product the additional compounds are prepared as follows:

EXAMPLE XII

3-Pipeidinecarboxamide, 1-[2-[bis(4-chlorophenyl)methoxy]ethyl]-, monohydrochloride, M.P. 214°-216° C.,

EXAMPLE XIII

3-Piperidinecarboxylic acid, 1-[2-[bis (4-fluorophenyl)methoxy]ethyl]-, monohydrochloride, M.P. 120°–122° C.,

EXAMPLE XIV

3-Piperidinecarboxylic acid, 1-[2-[bis (3,4-dichlorophenyl)methoxy]ethyl]-, hydrochloride, M.P. 166°–167° C.,

EXAMPLE XV

3-Piperidinecarboxylic acid, 1-[2-[bis (4-methylphenyl)methoxy]ethyl]-, ethyl ester, monohydrochloride, M.P. 137°–140° C.

EXAMPLE XVI

3-Piperidinecarboxylic acid, (R)1-[2-[bis(4-chlorophenyl)methoxy]ethyl]-, monohydrochloride, M.P. 182°–184° C.

EXAMPLE XVII

3-Pyridinecarboxylic acid, 1-[2-[bis-[4-(trifluoromethyl)phenyl]methoxy]ethyl]-1,2,5,6-tetrahydro-, monohydrochloride, M.P. 240°–244° C.

EXAMPLE XVIII

3-Piperidinecarboxylic acid, 1-[2-[bis-[4-(trifluoromethyl)phenyl]methoxy]ethyl]-, hydrochloride, M.P. 208°–215° C.

EXAMPLE XIX

3-Pyridinecarboxylic acid, 1-[2-[bis-(4-chlorophenyl)methoxy]ethyl]-1,2,5,6-tetrahydro, hydrochloride, M.P. 184°–185° C.

EXAMPLE XX

3-Piperidinecarboxylic acid, 1-[2-[bis[-(4-trifluoromethyl)phenyl]methoxy]ethyl]-,(-)monohydrochloride, (-)-, M.P. 218°–220° C.

EXAMPLE XXI

3-Piperidinecarboxylic acid, 1-[2-[bis-(4-chlorophenyl)methoxy]ethyl]-, methyl ester, monohydrochloride, M.P. 78°–80° C., monohydrate, M.P. 87°–89° C.

EXAMPLE XXII

3-Piperidinecarboxylic acid, 1-[2-[bis[-4-(trifluoromethoxy)phenyl]methoxy]ethyl]-, monohydrochloride, M.P. 151°–152° C.

EXAMPLE XXIII

3-Piperidinecarboxylic acid, 1-[2-[cyclohexyl(3,4-dichlorophenyl)methoxy]ethyl]-, hydrochloride, M.P. 160°–164° C.

EXAMPLE XXIV

3-Piperidinecarboxylic acid, 1-[2-[bis-(4-chlorophenyl)methoxy]ethyl]-4-hydroxy-, monohydrochloride, trans-, M.P. 120°–122° C.

EXAMPLE XXV

3-Piperidinecarboxylic acid, 1-[2-(triphenylmethoxy)ethyl]-, M.P.95°–98° C.

EXAMPLE XXVI

3-Piperidinecarboxylic acid, 1-[-[bis-(4-chloro-2-methylphenyl)methoxy]ethyl]-, monohydrochloride, +/−, M.P. 224°–225° C.

EXAMPLE XXVII

3-Piperidinecarboxylic acid, 1-[2-[(4-chlorophenyl)-2-thienylmethoxy]ethyl]-, M.P. 97°–105° C.

EXAMPLE XXVIII

3-Piperidinecarboxylic acid, 1-[2-[bis(4-metnylphenyl)methoxy]ethyl]-, hydrochloride, M.P. 125°–140° C.

EXAMPLE XXIX

3-Pyrrolidineacetic acid, 1-[2-[bis(4-chlorophenyl)methoxy]ethyl]-. (NMR) δ $CDCl_3$: 7.27 (S, 8H, aromatic), 5.38 (S, 1H, O—CH—), 3.65 (m, 2H, $CH_2CO_2H$), 3.05–2.0 (m, 8H, N—$CH_2CH_2$, C-2, C-5 pyrrolidine ring), 16 (m, 3H, C-3, C-4 pyrrolidine ring).

EXAMPLE XXX

3-Piperidinecarboxylic acid, 1-(4-propyldecyl)-. (NMR) δ $CDCl_3$: 3.15–2.50 (m, 7H, N—$CH_2$, C-2, C-3, C-6 piperidine), 2.10–1.05 (m, 23H, C-4, C-5 piperidine, side-chain alkyl), 1.0–0.75 (t, 6H, $CH_3$).

EXAMPLE XXXI

3-Piperidinecarboxylic acid, 1-(3-propylnonyl)-, monohydrochloride, M.P. 155°–157° C.

EXAMPLE XXXII

3-Piperidinecarboxylic acid, 1-[2-[(4-chlorophenyl)-2-furanylmethoxy]ethyl]- (Mixture of diastereomers), M.P. 48°–65° C.

EXAMPLE XXXIII

3-Pyridinecarboxylic acid, 1-[2-[bis(4-chlorophenyl)methoxy]ethyl]-1,2,3,6-tetrahydro-, methyl ester.

(NMR) δ $CDCl_3$: 7.27 (S, 8H, aromatic), 5.83 (m, 2H, C-4, C-5) 5.33 (S, 1H, O—CH),3.69 (S, 3H, $CO_2CH_3$), 3.58 (dd, 2H, J=5.9 Hz, C-6), 3.30 (m, 1H, C-3), 3.02 (bm, 2H, C-2) 2.89 (t, 2H, J=6.8 Hz, $NCH_2$, 2.76 (t, 2H, J=6.8 Hz, $CH_2$—O).

EXAMPLE XXXIV

3-Piperidinecarboxylic acid, 1-[2-[bis(4-chlorophenyl)methoxy]ethyl]-, hydrochloride (S) S(+) Enantiomer of Example XVI), M.P. 176°–183.5° C.

EXAMPLE XXXV

3-Pyrrolidineacetic acid, 1-[2-[bis(4-chlorophenyl)methoxy]ethyl]-, methyl ester.

(NMR) δ $CDCl_3$: 7.19 (S, 8H, aromatic), 5.38 (S, 1H, O—CH—), 3.58 (m, 2H, $CH_2CO_2$), 3.52 (S, 3H, $CO_2CH_3$), 2.95–1.95 (m, 8H, N—$CH_2CH_2$, C-2, C-5 pyrrolidine), 1.30 (m, 3H, C-3, C-4 pyrrolidine ring).

EXAMPLE XXXVI

3-Piperidinecarboxylic acid, 1-[2-[bis(4-chlorophenyl)methoxy]ethyl]-4-hydroxy-, monohydrochloride, cis-, M.P. 92°–100° C.

EXAMPLE XXXVII

3-Piperidinecarboxylic acid, 1-[2-[(4-chlorophenyl)-phenylmethoxy]ethyl]-, hydrochloride (5:6).

(NMR) δ CDCl$_3$: 7.29 (S, 9H, aromatic) 5.46 (S, 1H, O—CH), 4.05–3.9 (b, 2H, OCH$_2$) 3.8–1.1 (m, 11H, C-2, C-3, C-4, C-5, C-6, NCH$_2$—CH$_2$).

EXAMPLE XXXVIII

Piperidine, 1-[2-[bis(4-chlorophenyl)methoxy]ethyl]-, hydrochloride, M.P. 171°–173° C.

EXAMPLE XXXIX

Ethanone, 1-[1-[2-[bis(4-chlorophenyl)methoxy]ethyl]-3-piperidinyl]-, monohydrochloride, M.P. 91°–94° C.

EXAMPLE XL

4-Piperidinecarboxylic acid, 1-[2-[bis(4-chlorophenyl)methoxy]ethyl]-,ethyl ester, monohydrochloride, M.P. 149°–150° C.

EXAMPLE XLI

3-Pipeidinecarboxamide, 1-[2-[bis(4-chlorophenyl)methoxy]ethyl]-, monohydrochloride, M.P. 210.5°–212.5° C.

(NMR) δ D$_2$O: 7.38 (S, 8H, aromatic), 5.53 (S, 1H, O—CH—), 3.86 (bs, 2H, NH$_2$), 3.6–3.0 (bm, 9H, N—CH$_2$—CH$_2$, C-2, C-3, C-6 piperidine ring), 2.2–1.8 (bm, 4H, C-4,C-5 piperidine ring).

EXAMPLE XLII

3-Piperidinecarboxylic acid, 1-[2-(diphenylmethoxy)ethyl]-, ethyl ester.

NMR δ D$_2$O: 7.30 (m, 10H, aromatic), 5.38 (S, 1H, CH), 4.12 (q, 2H, J=7.2 Hz), 3.61 (t, 2H, J=6.0 Hz, NCH$_2$), 3.10 (m, 1H, C-3), 2.9–1.3 (m, 8H, C-2, C-4, C-5, C-6), 2.70 (t, 2H, J=6.0 Hz, CH$_2$), 1.24 (t, 3H, 5=7.2 Hz, CO$_2$CH$_2$CH$_3$).

EXAMPLE XLIII

3-Pyridinecarboxylic acid, 1-[2-[bis(4-chlorophenyl)methoxy]ethyl]-1,2,5,6-tetrahydro, methyl ester.

(NMR) δ CDCl$_3$: 7.30 (S, 8H, aromatic), 7.0 (m, 1H, C-4), 5.33 (S, 1H, O—CH), 3.73 (S, 3H, CO$_2$CH$_3$), 3.62 (t, 2H, J=5.9 Hz, CH$_2$—O), 3.25 (m, 2H, C-2), 2.79 (t, 2H, J=5.9 H, N—CH$_2$), 2.61 (dd, 2H, J=5.7 Hz, C-6), 2.35 (m, 2H, C-5).

EXAMPLE XLIV

3-Piperidinemethanol, 1-[2-[bis(4-chlorophenyl)methoxy]ethyl]-, monohydrochloride, M.P. 160°–162° C.

EXAMPLE XLV

3-Piperidinecarboxylic acid, 1-(4,4-diphenylbutyl)-, methyl ester, monohydrochloride.

(NMR) δ d$_6$-DMSO: 7.29 (S, 10H, aromatic), 3.93 (t, 1H, CH$_2$—CH), 3.60 (S, 3H, CO$_2$CH$_3$) 3.5–2.5 (bm, 7H, NCH$_2$, C-2, C-3, C-6 piperidine ring) 2.18–1.5 (bm, 8H, NCH$_2$—(CH$_2$)$_2$, C-4, C-5 piperidine ring).

EXAMPLE XLVI

3-Piperidinecarboxylic acid, 1-[3-[(diphenylmethoxy)]propyl]-.

(NMR) δ CDCl$_3$: 7.28 (S, 10H, aromatic), 5.39 (S, 1H, O—CH), 3.52 (m, 2H, O—CH$_2$), 3.2–2.3 (bm, 7H, N—CH$_2$, C-2, C-3, C-6 piperidine ring), 2.1–1.5 (bm, 6H, C-4, C-5 piperidine ring, N—CH$_2$—CH$_2$).

I claim:
1. 3-Piperidinecarboxylic acid, 1-[2-[bis[(4-trifluoromethyl)phenyl]methoxy]ethyl]-, monohydrochloride, (−)-.
2. 3-Piperidinecarboxylic acid, 1-[2-[bis(4-chlorophenyl)methoxy]ethyl]-, methyl ester, monohydrochloride.
3. 3-Piperidinecarboxylic acid, 1-[2-[bis[4-(trifluoromethoxy)phenyl]methoxy]ethyl]-, monohydrochloride.
4. 3-Piperidinecarboxylic acid, 1-[2-[cyclohexyl-(3,4-dichlorophenyl)methoxy]ethyl]-, hydrochloride.
5. 3-Piperidinecarboxylic acid, 1-[2-[bis(4-chlorophenyl)methoxy]ethyl]-4-hydroxy-, monohydrochloride, trans-.
6. 3-Piperidinecarboxylic acid, 1-[2-(triphenylmethoxy)ethyl]-.
7. 3-Piperidinecarboxylic acid, 1-[2-[bis(4-chloro-2-methylphenyl)methoxy]ethyl]-, monohydrochloride.
8. 3-Piperidinecarboxylic acid, 1-[2-[(4-chlorophenyl)-2-thienylmethoxy]ethyl]-.
9. 3-Piperidinecarboxylic acid, 1-[2-[(4-chlorophenyl)-2furanylmethoxy]ethyl].
10. 3-Pyridinecarboxylic acid, 1-[2-[bis(4-chlorophenyl) methoxy]ethyl-1,2,3,6-tetrahydro-, methyl ester.
11. 3-Piperidinecarboxylic acid, 1-[2-[bis(4-chlorophenyl)methoxy]ethyl]-, hydrochloride.
12. 3-Piperidinecarboxylic acid, 1-[2-[bis(4-chlorophenyl)methoxy]ethyl]-4-hydroxy-, monohydrochloride, cis-.
13. 3-Piperidinecarboxylic acid, 1-[2-[(4-chlorophenyl)phenylmethoxy]ethyl]-, hydrochloride (5:6).
14. 4-Piperidinecarboxylic acid, 1-[2-[bis(4-chlorophenyl)methoxy]ethyl]-, ethyl ester, monohydrochloride.
15. 3-pipeidinecarboxamide, 1-[2-[bis(4-chlorophenyl)methoxy]ethyl]-,monohydrochloride, (s)(s)(+) enantiomer.
16. 3-Pyridinecarboxylic acid, 1-[2-[bis(4-chlorophenyl)methoxy]ethyl]-1,2,5,6-tetrahydro, methyl ester.

* * * * *